(12) United States Patent
Davydov et al.

(10) Patent No.: US 10,117,633 B2
(45) Date of Patent: Nov. 6, 2018

(54) METHOD AND APPARATUS FOR CHARACTERIZATION OF X-RAY ENERGY OUTPUTS OF MEDICAL X-RAY GENERATORS

(71) Applicant: Iyov Intellectual Properties, Grand Cayman (KY)

(72) Inventors: Albert Davydov, Forest Hills, NY (US); Peter Usov, Belle Mead, NJ (US)

(73) Assignee: Albert Davydov, Forest Hills, NY (US)

( * ) Notice: Subject to any disclaimer, the term of this patent is extended or adjusted under 35 U.S.C. 154(b) by 178 days.

(21) Appl. No.: 15/244,416

(22) Filed: Aug. 23, 2016

(65) Prior Publication Data

US 2018/0055475 A1    Mar. 1, 2018

(51) Int. Cl.
*A61B 6/00* (2006.01)
(52) U.S. Cl.
CPC .............. *A61B 6/586* (2013.01); *A61B 6/461* (2013.01); *A61B 6/542* (2013.01)

(58) Field of Classification Search
None
See application file for complete search history.

(56) References Cited

U.S. PATENT DOCUMENTS

2016/0095561 A1\* 4/2016 Tamura .................. A61B 6/032
378/62

\* cited by examiner

*Primary Examiner* — Hoon Song
(74) *Attorney, Agent, or Firm* — Anna Vishev

(57) ABSTRACT

A method for continuously evaluating an X-ray unit. The method includes placing an X-ray sensor converter having a photo diode and a scintillation crystal in a path of an X-ray beam emitted by the X-ray unit, using the X-ray sensor converter to convert an X-ray beam energy into an electric signal, providing an amplifier connected to the X-ray sensor converter, conveying the electric signal from the X-ray sensor converter to the amplifier, amplifying the electric signal with the amplifier, and measuring a spectrum of the X-ray tube energy by continuously sampling and quantifying the amplified electric signal.

6 Claims, 2 Drawing Sheets

METHOD AND APPARATUS FOR CHARACTERIZATION OF X-RAY ENERGY OUTPUTS OF MEDICAL X-RAY GENERATORS

BACKGROUND OF THE INVENTION

This application and its disclosure generally relate to the field of precise and continuous (during a life time of an X-ray system) measurement of the Practical Peak Voltage (PPV) in a radiological practice.

Peak kilovoltage (kVp) is the maximum voltage applied across an X-ray tube. It determines the kinetic energy of the electrons accelerated in the X-ray tube and the peak energy of the X-ray emission spectrum. The actual voltage across the tube may fluctuate from an exposure to an exposure with the same, time, KvP and mA setting. Further, the age of a particular machine has a significant effect on mean kVp accuracy. Determination of the peak kilovoltage (kVp) applied to a particular X-ray tube plays a fundamental role in the evaluation of the system calibration and performance, and patient' cumulative exposure dose quantification. Accordingly, it is very important to accurately determine the peak kilovoltage (kVp) accuracy of an individual X-ray unit during performance at each time the unit is used and to compare and monitor its values.

It is well-known in the industry, that small variations in kVp values may produce significant increases in patient absorbed doses due to the approximately squared dependence between the air kinetic energy released per unit of mass (air kerma) and kVp. The relation between the variation in the tube voltage and the variation of the absorbed dose depends upon the part of the body being irradiated and the used kVp range. Martin et al., for example, have evaluated anteroposterior radiographic views of the abdomen and reported a mean variation of the equivalent dose absorbed by the liver of 3.5% by kVp unit in the range between 60 and 120 kVp, 1%/kVp between 90 and 100 kVp and 13%/kVp between 60 and 70 kVp. Another study, described in Fung et al., has demonstrated that a variation in the voltage applied to the tube also produces a significant contribution to the patient absorbed dose due to the scattered beam.

The practical peak voltage (PPV) has been adopted as the reference measuring quantity for the x-ray tube voltage. However, the majority of commercial kV-meter models measure the average peak voltage, U(P); the average voltage, U; the effective voltage, U(eff); or the maximum peak tube voltage, U(P).

Most of the conventional measuring equipment are not capable of accurately measuring X-ray radiation due to the relatively low energy emitted. Traditionally, cumbersome ionization chambers are used for measuring X-ray radiation. They are big and require lots of equipment. X-ray energy contrast is significantly lower during exposures through the use of ionization chambers resulting in a very low contrast quality of an X-ray image. Radiologists either repeat the procedure trying to increase the quality of an image by increasing the kVp. That increases the radiation exposure. The inventors of the present application evaluated a utilization of a dose monitoring equipment and found that all studied, small and large facilities in NY and NJ, are currently not utilizing any means of registration of X-ray energy during an X-ray imaging procedure. They have also evaluated ten X-ray facilities in NY and exposed 10 X-ray emissions at specific setting for every spinal part. Total 40 X-rays were exposed at each X-ray machine corresponding 10 for cervical, 10 for thoracic, 10 for lumbar and 10 for lumbar-sacral anatomies. The result of the findings was as follows: 1) all of them produced different outputs readings with the same KvP and mA and time settings; 2) Not only they were producing different results on the same settings, but also the results within the settings produced different readings. These differences led to a conclusion that X-ray exposures are producing uncontrolled and unpredictable energies during every X-ray image procedure. This led the inventors to conclude that these energy outputs variations create health hazard conditions for the patients of the radiology facilities currently receiving uncontrolled, dangerously high and, most importantly, unknown and un-monitored levels of radiation exposures.

SUMMARY OF THE INVENTION

It is an object of the present invention to provide a method and system capable of evaluating the practical peak voltage (PPV) determined from the voltage waveform applied to X-ray tubes.

In its general aspect, the invention is a method for continuously (during X-ray equipment's entire life time) evaluating an X-ray unit. The method includes placing an X-ray sensor converter having a photo diode and a scintillation crystal in a path of an X-ray beam emitted by the X-ray unit, using the X-ray sensor converter to convert an X-ray beam energy into an electric current, providing an amplifier connected to the X-ray sensor converter, conveying the electric current from the X-ray sensor converter to the amplifier, amplifying the electric current with the amplifier, and measuring a spectrum of the X-ray tube energy by continuously sampling and quantifying the amplified electric current.

In one specific aspect, the step of measuring the spectrum further includes presenting discrete values of the amplified electric signal as a continuous waveform over a predetermined period of time. This continuous waveform can then be studied to determine potential malfunctions in the X-ray unit and/or the precise exposure dosage for a particular patient.

BRIEF DESCRIPTION OF THE DRAWINGS

The invention is illustrated by way of examples which are not a limitation, and the figures of the accompanying drawings in which references denote corresponding parts, and in which.

DETAILED DESCRIPTION OF THE INVENTION

Figure 1:
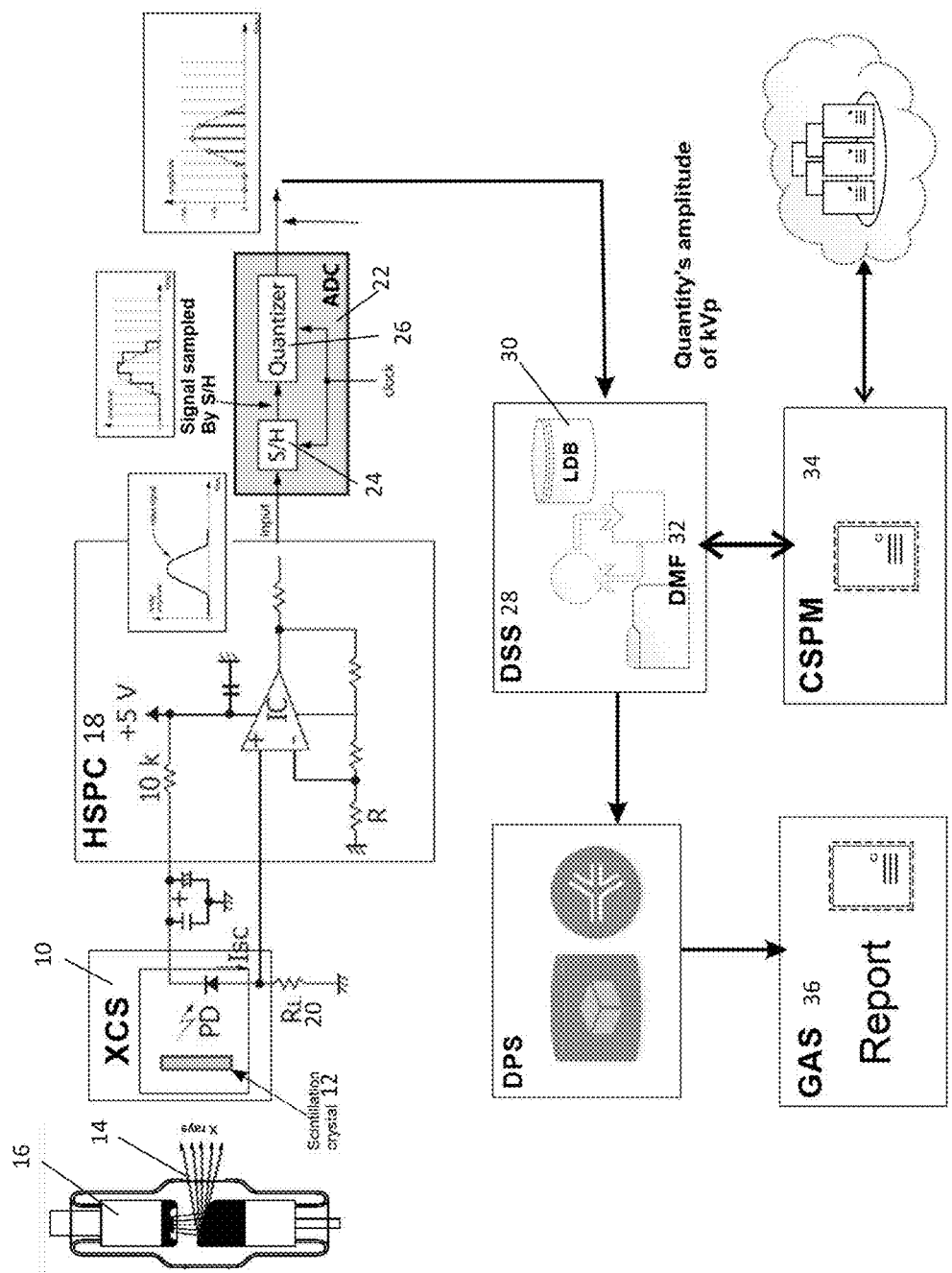
FIG. 1 is a schematic diagram of characterization of X-Ray energy outputs.

As illustrated in the attached FIG. 1, an X-ray Sensor Converter XSC 10, having a Si-PIN photo diode PD and a Cesium Iodide (Thallium doped) scintillation crystal 12, is placed in the X-ray beam 14 emitting from an X-ray tube 16. The scintillation crystal 12 absorbs the energy of the X-ray beam and re-emits the absorbed energy in the form of light (i.e., photons), which is then converted by the photo diode PD into an electric signal (i.e., electrons) via the photoelectric effect. XSC 10 is thus used to digitize the spectrum emitted from the X-ray tube energy.

The electric signal is then supplied from the XSC 10 to a high speed photodetector circuit HSPC 18. The HSPC 18 uses load resistance RL 20 to convert the electric signal from XSC 10 (with a reverse voltage applied) to a first voltage. A high speed operational amplifier is then utilized to amplify the first voltage. The signal carrying the amplified first voltage is then supplied to analog-to-digital converter ADC 22. In the preferred embodiment, the ADC 22 is a digital oscilloscope system, which includes a sampling module S/H 24 and a quantization module 26. The modules 24 and 26 convert a continuous physical quantity of X-ray energy, i.e., the signal voltage, to a digital number that represents the quantity's amplitude of this signal, which is then recorded by this digital oscilloscope system. The sampling performed by module 24 and quantization performed by module 26 of the ADC 22 allows the system of the present invention to record 1 mega-sample of tube energy per second, and, consequently, allows the Pkv to be registered in small incremental intervals of time (~1 μS). This digital oscilloscope system allows for the discrete voltage signals to be observed as a continuous waveform over a long period of time.

Digital information obtained in this manner is then processed by a digital storage system DSS 28, which preferably includes at least one local database LDB 30, and stores the obtained digital information of X-ray tube energy signal (as a discrete-time signal) for a particular X-ray tube study, for example, on a digital media as a digital media file DMF 32.

Typical sampling rates of X-ray outputs energy obtained using the method of the present invention are higher than can currently be recorded on a permanent medium, therefore DSS 28 preferably stores the obtained data on a solid state memory at a high sampling rate and then transfers it to a permanent memory later at a slower rate. This approach is necessary when sampling rates exceed 1 Msr/s. The sampling rates attainable with this approach are limited only by the speed of ADC 22.

Data processing software DPS 32 reads data of each X-ray study from the digital media for further processing such as analyzing, reporting and issuing emergency warnings. Raw and analyzed data is preferably stored in the LDB 30. Thus, the intensity-time relationship of the x-ray beam for any particular individual X-ray unit can be retrieved and compared at any time. The x-ray waveform can then be observed to find a wide variety of problems present in the studied X-rays.

Cloud storage provider and manager CSPM 34 connects the apparatus to the central database when internet connection is present (Wi-Fi or wired). It sends the data of a particular X-ray study to the central database and retrieves the previously stored records for any particular X-ray machine for general analysis via a general analysis system GAS 36.

The big advantage of this method is that by analyzing a series of X-ray studies for the same X-ray machine, calculations of kVp accuracy and stability of individual x-ray unit during the entire lifetime of its operation can be achieved. Thus, the present method allows for a continuous study of a particular X-ray unit over a long period of time, rather than at a random discrete time period, generating a more accurate data of the radiation exposure at this particular unit.

An X-Ray output oscilloscope is included in the present system to calibrate and troubleshoot any problems with X-ray generators.

Figure 2:
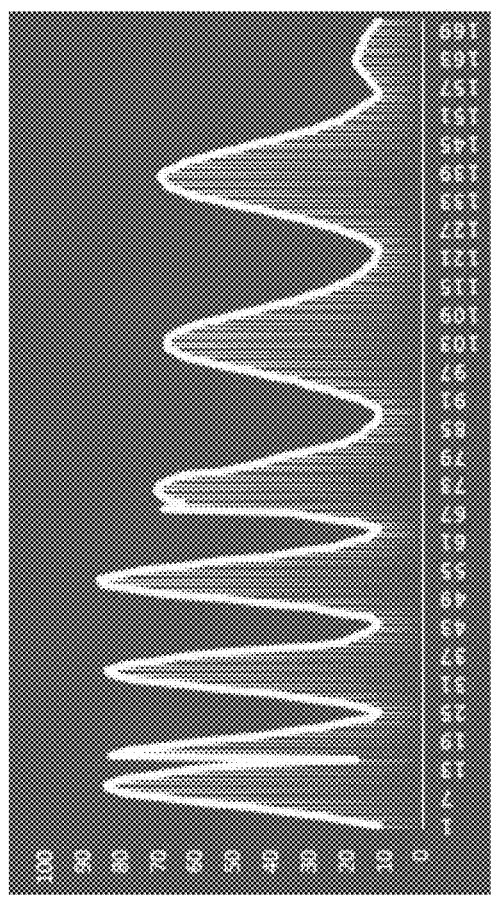
FIG. 2 is the X-ray outputs graph.

One of the advantages of the present system is that it can graphically and continuously show an output of a particular X-Ray unit, as shown, for example, in FIG. 2. Where a conventional kVp meter may show an average or a random kVp, the oscilloscope reveals a precise nature of the kVp, i.e., a continuously oscillating kVp. In other words, the present system measure a precise shaping and timing of the kVp pulse that is extremely important especially in an exposure determination.

In accordance with the preferred embodiment, the system measures the following X-Ray parameters: peak kilovoltage (kVp); effective kV; mAs; exposure doses; dose rates; and exposure time. The system further records pulses and waveforms, test data and data analyses.

The value of an x-ray tube kVp is the most critical determinant. A small variation in this variable will have a greater effect on the final radiographic or fluoroscopic image than will any equivalent variation in any of the other parameters such as tube current (mA), exposure time or target film distance. The x-ray intensity reaching the image receptor after the beam passes through the patient varies approximately as the fifth power of kVp. The kVp affects not only the intensity of the energy reaching the image receptor but also the subject contrast of the image.

Variations between a specified (i.e., what the value of kVp is supposed to be for a particular unit) and an actual kVp occur for several reasons:

The X-ray generator was not set properly upon installation;

Excessive power line voltage drops;

Tube current drifts have changed the voltage drop across the high voltage transformer secondarily. The tube voltage has changed even though the primary voltages have remained constant. (Line voltage compensator circuits must be set properly.)

Component Failure.

The system of the present invention provides a measurement of the peak electrical potential across the X-ray tube during its operation. The system measures and records kVp each time an X-ray energy is emitted. Thus, the system allows its operator to detect and analyze variations of the actual kVp value in real time, and to diagnose the underlying problems with the X-ray generator as they occur.

The effective kV is the kV that will give the same contrast as a DC exposure with an ideal ripple, while the peak kV is the largest kV over the duration of the exposure.

If the time values of exposure are correct and if the mA settings are within calibration limits, then exposures of the same mAs value should yield the same quality of radiograph, and the same cumulative exposure quantifications provided that there is the same patient's size. If the preceding test confirmed the correctness of the time values then the images of the step wedges should be the same for each exposure. This test may be done concurrently with the IVC above by exposing the step wedge with the top. High sensitivity of X-ray sensor of apparatus allows accurate measurement at electrical currents down to approximately 10 mA. Normal accuracy is obtained at 15 to 200 mA.

Industry standards and some regulations use the concept of effective dose in which all the individual doses to the irradiated organs or parts of the body is multiplied by a factor and then added together. The resulting value may not exceed the dose limit for the effective dose that a patient is allowed to receive. Dose is a measure of the X-Ray intensity integrated for the entire X-Ray exposure time over the (8 mm×8 mm) 64 mm$^2$ area. The dose equivalent of a patient in the X-Ray beam, so far as body dose or effective dose, is the comprehensive dose for the organ or body. This can be estimated by deducing the area of the X-ray beam in mm$^2$ as constant over the entire area.

Since, measurements are very sensitive to the distance from the X-ray head (because the X-ray intensity change is proportional to the square of the distance from the X-ray head), the distance is subject to the initial conditions.

To measure a dose, the beam must operate for a certain period of time. The dose rate represents the measured dose for the amount of time required to complete the dose measurement. The dose rate is equal to the measured dose mathematically scaled by exposure time and is given as mR and uGy per second. A measurement of the amount of radiation measured at a site over a specific period of time, produces the concept of "dose". Not all the radiation particles generated during the x-ray are used to produce the resulting images, and because radiation can cause damage to the human body, medical personnel try to get the best possible image with the smallest possible dose of radiation. The concept of "dose" can mean different things according to the where and how the measurement is made, particularly with respect to the site where the dose is measured.

Because the system of the present invention continuously measures the actual kVp of a particular X-ray tube, it produces a dose graph, which instantaneously shows an accurate dose for the entire X-ray exposure time.

The output and beam quality are evaluated using a fixed and reproducible geometry. The actual output of an X-ray system may change over time as a result of component failure, absence of a required filter, drift from calibrated values or other causes. The beam quality test conducted by the present system verifies that the half-value layer is sufficient to reduce patient exposure to low-energy radiation and assures that filters, which may have been removed for mammography or tube inspection, are in place for normal radiography.

This present system also measures the effective value of the maximum and peak accelerating voltage that occur during any part of the X-Ray exposure and reads and displays the peak effective value of the accelerating voltage (kVp effective) during the rest of the X-ray exposure.

Accurate measurement and verification of the exposure time is very important, especially where an X-ray machine is not supplied with an AEC system (Automatic Exposure Control also called Photo Timing), or where the study of a patient is conducted without AEC X-ray exposures. The system of the present invention measures the exposure time each time an X-ray measurement is made and displays the exposure time in milliseconds (ms).

The present system is also designed to accurately measure even short exposure times in order to minimize wear on the X-ray head and exposure to service personnel.

Similarly, the present system is designed to accurately measure scattered radiation exposure by changing the sensitivity of the sensors to minimize potential X-ray exposure to service personnel. In this case, more than one device in various locations depending on the need can be used to determine and measure scattered radiation exposure.

Some x-ray units, particularly older models take a relatively long time to reach peak exposure. In this case, the system also includes an auto waiting system for postponing the start of X-ray measurements.

Recorded data is processed and reported in several aspects. In the preferred embodiment, the outputs of X-ray energy are represented in a graph where the X axis is time (mks) and the Y axis is kVp value.

The analysis of the presented graph allows defining the following defects of the equipment:
High voltage source and high voltage transformer;
High voltage rectifier;
Thermal overload detector;
Pulse duration timer and Automatic exposure control (AEC);
Tube Failure: X-ray tubes can fail in a number of different ways. Most tube failures occur as the result of thermal wear on the internal component parts. The wear usually develops over a period of time. However, an instantaneous load significantly above the tube rating can cause a tube to fail immediately. Common types of tube failure include worn rotor bearings, a cracked or pitted anode, gassing of the tube, and an open cathode filament; and
Aluminum Filter Failure.

In the preceding specification, the invention has been described with reference to specific exemplary embodiments thereof. It will however, be evident that various modifications and changes may be made thereto without departing from the broader spirit and scope of the invention as set forth in the claims that follow. The specification and drawings are accordingly to be regarded in an illustrative manner rather than a restrictive sense.

We claim as follows:

1. A method for continuously evaluating an X-ray unit, the method comprising the steps of:
   placing an X-ray sensor converter having a photo diode and a scintillation crystal in a path of an X-ray beam emitted by the X-ray unit;
   using the X-ray sensor converter to convert an X-ray beam energy into an electric signal;
   providing an amplifier connected to the X-ray sensor converter;
   conveying the electric signal from the X-ray sensor converter to the amplifier and amplifying the electric signal with the amplifier;
   measuring a spectrum of an energy emitted by the X-ray unit by continuously sampling and quantifying the amplified electric signal, said step of measuring the spectrum comprising presenting discrete values of the amplified electric signal as a continuous waveform over a predetermined period of time;
   displaying the results of the step of measuring the spectrum of the X-ray tube as a continuous graph representing the continuous waveform of variations of an X-ray voltage; and
   analyzing the continuous graph to determine a specific voltage emitted by the X-ray tube over a particular time interval.

2. The method according to claim 1, further comprising a step of evaluating performance of the X-ray tube using results of said step of analyzing the continuous graph.

3. The method according to claim 2, wherein said step of evaluating performance comprises detecting at least one of high voltage source and high voltage transformer malfunction, high voltage rectifier malfunction, thermal overload detector malfunction, pulse duration timer and automatic exposure control malfunction, tube malfunction and aluminum filter malfunction.

4. The method according to claim 3, further comprising issuing an emergency warning to an X-ray operator when one of said malfunctions is detected.

5. The method according to claim 1, further comprising a step of calculating a precise radiation exposure dosage for a particular patient using results of said step of analyzing the continuous graph.

6. A method for continuously evaluating an X-ray unit, the method comprising the steps of:
   placing an X-ray sensor converter having a photo diode and a scintillation crystal in a path of an X-ray beam emitted by the X-ray unit;

using the X-ray sensor converter to convert an X-ray beam energy into an electric signal;
providing an amplifier connected to the X-ray sensor converter;
conveying the electric signal from the X-ray sensor converter to the amplifier and amplifying the electric signal with the amplifier;
measuring a spectrum of an energy emitted by the X-ray unit by continuously sampling and quantifying the amplified electric signal;
providing a unified statistical global monitoring system; and
enabling said statistical global monitoring system to gather, store, compare, process, and report about a particular X-ray system malfunction on a global scale.

* * * * *